United States Patent [19]

Taylor et al.

[11] Patent Number: 4,467,206

[45] Date of Patent: Aug. 21, 1984

[54] METHOD AND APPARATUS FOR THE IRRADIATION OF FLUIDS

[75] Inventors: John A. Taylor, Furlong; Richard F. Conyne, Rushland, both of Pa.

[73] Assignee: Extracorporeal Medical Specialties, Inc., King of Prussia, Pa.

[21] Appl. No.: 330,535

[22] Filed: Dec. 14, 1981

[51] Int. Cl.³ ............................................. G01N 21/00
[52] U.S. Cl. .................................. 250/435; 250/438; 422/24
[58] Field of Search ..................... 250/435, 438; 604/4; 128/395, 398; 422/44, 24

[56] References Cited

U.S. PATENT DOCUMENTS 3,998,591 12/1976 Eckfeldt ............................... 422/86
4,321,057 3/1982 Buckles ............................... 422/58

Primary Examiner—Bruce C. Anderson
Attorney, Agent, or Firm—Lawrence D. Schuler

[57] ABSTRACT

Device, apparatus, and method for the irradiation of fluids, especially physiological fluids such as blood. The device comprises a hollow casing having two end walls, at least one element adapted to transmit radiant energy disposed within said casing with an end thereof being secured in one of the end walls, and an inlet and an outlet in said casing between the end walls. The outer peripheral surface of the end portion of the element secured in the end wall is contacted by a material whose refractive index is equal to or less than the refractive index of the element. Preferably, the device employs a plurality of radiant energy transmitting elements in the form of fibers. Apparatus includes the aforementioned device and means for directing radiant energy onto the element(s) for transmitting radiant energy. Method for irradiating a fluid comprises providing the aforementioned device, directing radiant energy onto the radiant energy transmitting element(s) of said device, introducing fluid to be irradiated into the interior of the casing, and withdrawing said fluid from said casing.

56 Claims, 8 Drawing Figures

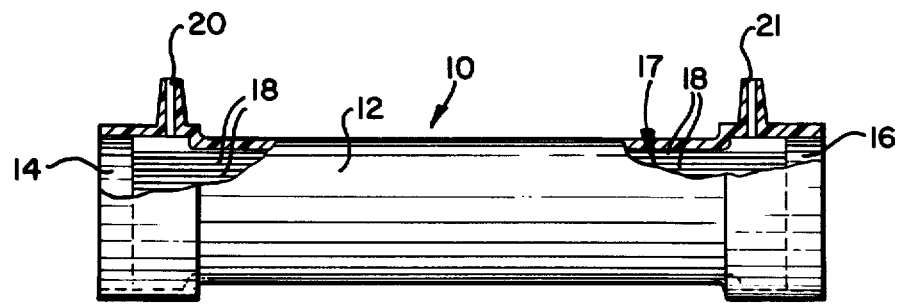
FIG. 1
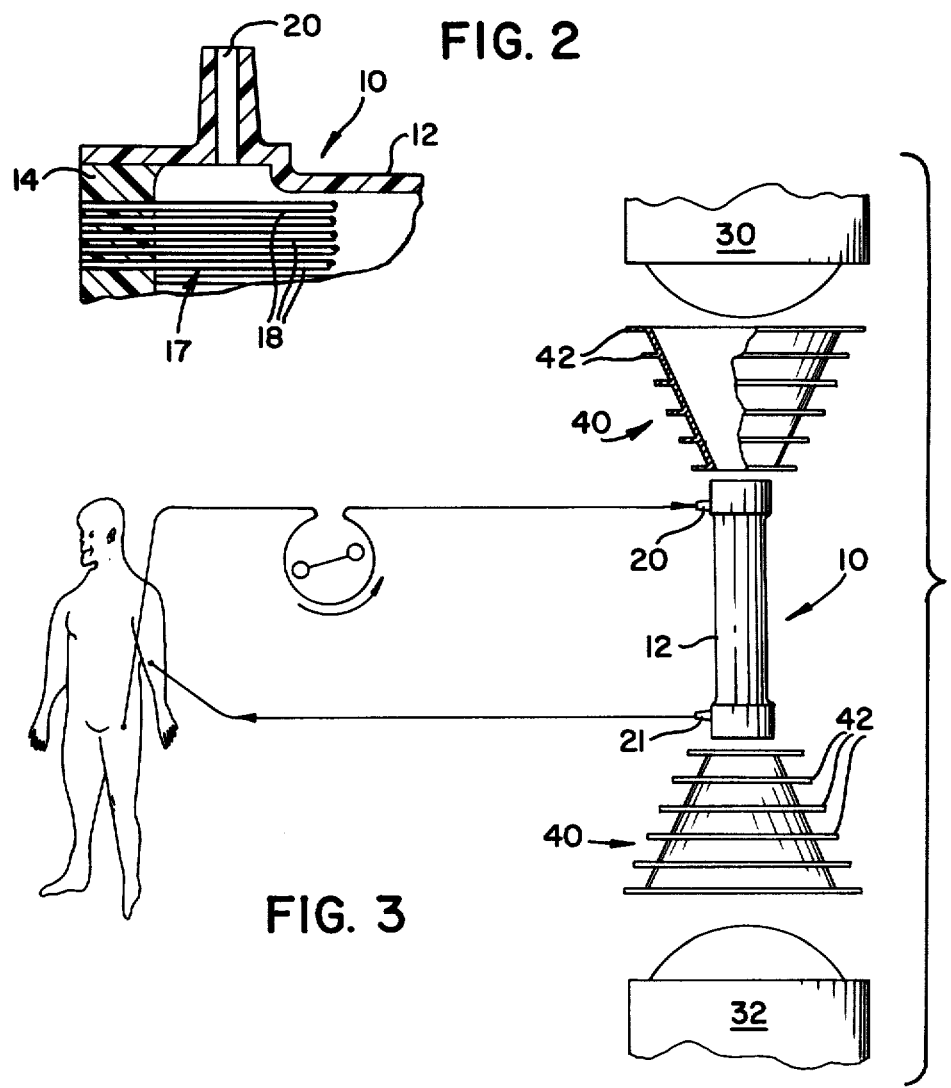
FIG. 2
FIG. 3

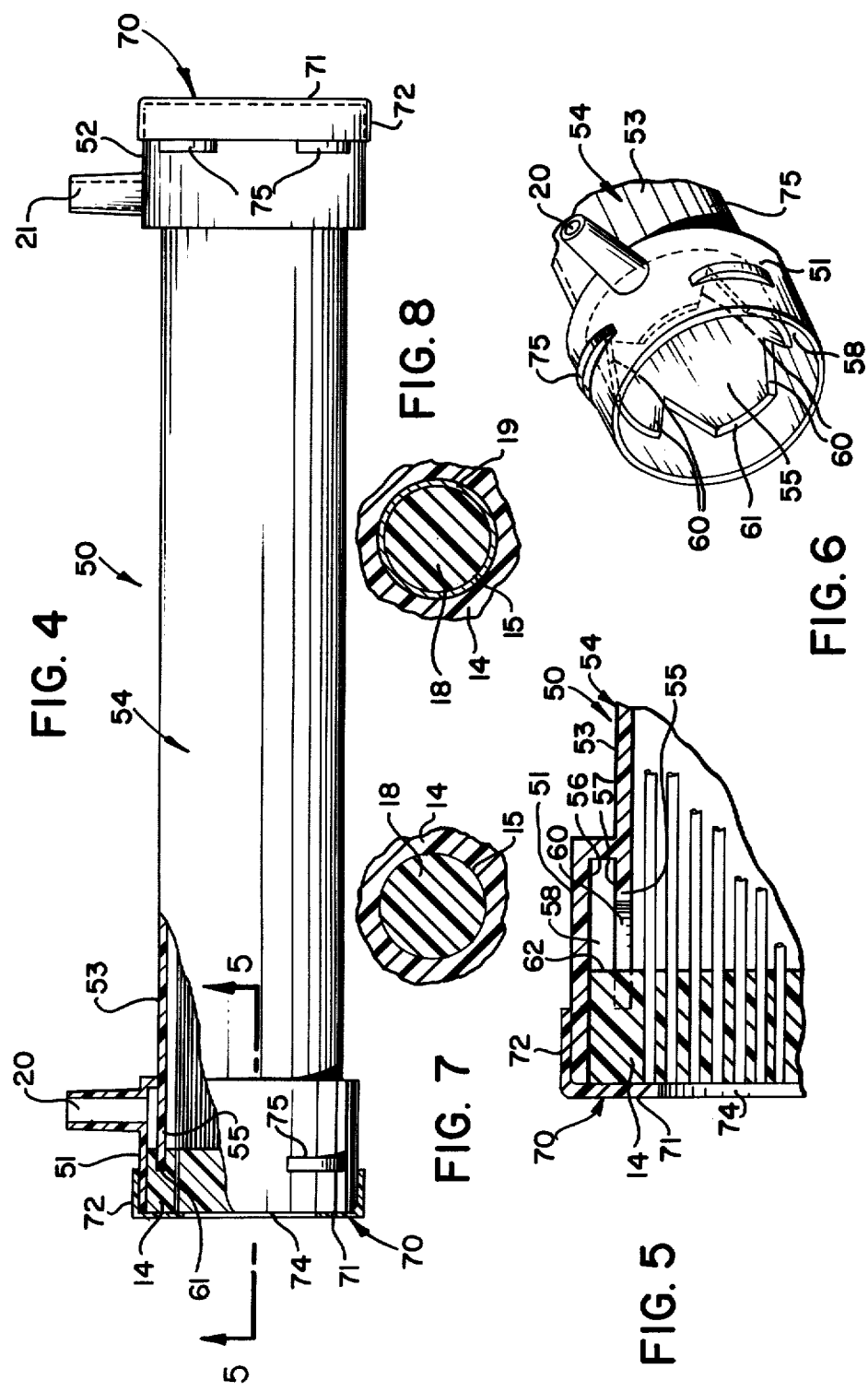

METHOD AND APPARATUS FOR THE IRRADIATION OF FLUIDS

FIELD OF THE INVENTION

The present invention relates generally to the irradiation of fluids. More particularly, the invention relates to an improved method and apparatus for irradiating fluids, especially physiological fluids such as blood. The apparatus includes a device which preferably has a plurality of elements adapted to transmit radiant energy from a source which is preferably located externally of the device and which may be used to effect irradiation of fluids contained therein or flowing therethrough.

BACKGROUND OF THE INVENTION

Radiation is employed in a variety of scientific and medical applications. For example, it is well known that certain polymerization reactions may be initiated by, for example, electron beam radiation or ultraviolet radiation. Such radiation initiated polymerization reactions are most successfully employed when it is desired to polymerize relatively thin films of monomer or prepolymer. Efforts to polymerize thicker films by this method, however, are often unsuccessful. This is because the radiation directed at the upper surface of the film is absorbed by the mixture of monomer or prepolymer and the newly formed polymer at or near the upper surface of the film and is thus not available for initiating polymerization of the monomer or prepolymer in the middle and bottom layers of the film. In addition to polymerization reactions, there are many other chemical reactions, e.g. those involving the synthesis of organic compounds, which are known to be catalyzed by ultraviolet or other irradiation.

As disclosed in U.S. Pat. No. 3,683,183 (Vizzini et al), blood and lymph have been extracorporeally irradiated in order to suppress immune antibody response to transplants and in order to manage some forms of leukemia. In European Pat. application No. 107,540, filed Dec. 3, 1980 and published on June 17, 1981 as U.S. Pat. publication No. 30,364, there is disclosed a method for the reduction of the functioning lymphocyte population in the blood supply of a human subject. The disclosed method involves first withdrawing blood from the subject, then irradiating the blood with ultraviolet light in the presence of 1 nanogram to 100 micrograms/ml. of dissolved psoralen that is activated by the irradiation and forms photoadducts with DNA. The psoralen is thus bonded to the nucleic acid of the lymphocytes so that their metabolic processes are inhibited. The irradiated blood is returned to the subject.

Many prior art irradiating devices, especially those used in medical applications, are large, cumbersome to use, and expensive to produce. The method disclosed in the aforementioned European Patent Application involves the treatment of blood at an irradiation station consisting of an irradiation chamber and a radiation source. In one disclosed embodiment, the chamber comprises a coil of tubing (e.g. polyvinylchloride tubing of the kind commonly used for administering standard intravenous solutions) which has been flattened to give it the cross-sectional form of an elongated ellipse. It is stated that the highly flattened cross-section of the coil allows for good exposure of the flowing blood to the incident radiant energy. It is believed difficult and cumbersome to treat a fixed volume of liquid, like blood, with the apparatus shown in European Pat. application No. 107,540. First of all, the apparatus would appear to be characterized by high pressure drops during use. If it is desired to treat a specified volume of material and it is necessary, in order to obtain high radiation efficiency, to provide a radiation chamber of quite limited thickness or depth, then the apparatus tends to be bulky and cumbersome. The bulk of the apparatus might be reduced by increasing the thickness or depth of the radiation chamber through which the blood flows, but this approach reduces radiation efficiency due to radiation extinction. It is possible to retain the limited thickness or depth of the radiation chamber, thus maintaining radiation efficiency, and at the same time reduce the overall bulk of the apparatus; this approach, however, would necessitate an undesirable increase in the time needed to irradiate a fixed volume of material. This increased time factor is especially undesirable when extracorporeally circulating blood is being treated.

SUMMARY OF THE INVENTION

In accordance with the present invention there is provided a device for irradiating a fluid flowing therethrough, said device being compact, very easy to use, and relatively inexpensive to produce. The device can be made so as to have a limited volume; this is especially important in processes involving the extracorporeal radiation of blood where it is desired to minimize the volume of the patient's blood which is outside the body at any one time. At the same time, the device of the present invention has a large surface area over which the material to be treated is exposed to the desired radiant energy and this large surface area results in high radiation efficiency. Finally, the device of the invention is characterized by low pressure drops during use.

The device of the invention comprises a hollow casing having first and second end walls and an inlet and outlet between those end walls. There is disposed within said casing at least one element adapted to transmit radiant energy into the hollow interior of the casing from a source which is preferably outside the casing. The radiant energy transmitting element has a first end and a second end, the first ends of this element preferably being secured in one of the end walls of the device. The second end of this element may be secured in the other of the end walls of the device. An end wall may be formed and the end or ends of the element for transmitting radiant energy simultaneously secured therein, by a potting technique which can be carried out manually or mechanically, as by the centrifugal potting processes of the type commonly used in the production of hollow fiber artificial kidneys. Preferably, the device comprises a plurality, and even more preferably a large plurality, of the radiant energy transmitting elements.

The elements adapted for transmitting radiant energy may be in the form of parallel plates, rods or hollow fibers. Of these, fibers are most preferred for use as the radiant energy transmitting elements in a device intended for the irradiation of physiological fluids such as blood.

In order for radiant energy from a source to be conducted most efficiently (that is, with a minimum loss of energy by scattering) by the radiant energy transmitting element or elements into the interior of the casing where, as will be seen later herein, the radiant energy is thereafter distributed to the fluid to be irradiated, it is preferred that the outer peripheral surface of the end portion of each element which is to be secured in an end wall at which radiant energy will be directed be contacted by a material whose refractive index is equal to or lower than the refractive index of the element itself. The aforementioned refractive index relationship can be most readily and conveniently achieved by forming the end wall in which the end portion of the radiant energy transmitting element is secured from a material whose refractive index is equal to or lower than the refractive index of the element itself. Alternatively, if it is desired to have an end wall whose refractive index is higher than the refractive index of the element itself, the aforementioned refractive index relationship can be achieved, and radiation transmitted most efficiently, by using a radiant energy transmitting element whose end portion which is to be secured in the end wall is coated with a material whose refractive index is lower than the refractive index of the element itself. In order to transmit radiant energy most efficiently, the important thing is to insure that the outer peripheral surface of the secured end portion of the radiant energy transmitting element be contacted by a material, which can be the end wall material itself or a coating on the end portion of the element, whose refractive index is equal to or lower than the refractive index of the element itself.

In accordance with another aspect of the present invention, there is provided apparatus for irradiating fluids. This apparatus includes a device having a hollow casing with a first end wall, a second end wall, an inlet and an outlet, and at least one element adapted to transmit radiant energy disposed within said casing; and means for directing radiant energy on to said one end of said element.

The apparatus may further include one or more means for collimating radiant energy from an external source and directing said collimated radiant energy onto the ends of the aforementioned radiant energy transmitting element(s). This collimating device is preferably in the form of a truncated cone and has externally located, heat conductive fins for dissipation of the heat generated by the impinging radiant energy. The collimating device can additionally include a focusing lens (particularly one made of quartz) and/or light filters to provide energy having a desired wavelength or wavelength band. The apparatus may also include fan for blowing air across the collimating device in order to increase the efficiency of cooling. The apparatus may be used for the treatment, on either a batch or continuous basis, of fluids with radiant energy.

BRIEF DESCRIPTION OF THE DRAWINGS

The present invention will be more clearly understood by reference to the accompanying drawings in which:

FIG. 1 is a perspective view, with some portions cut away and some parts shown in cross-section, of one embodiment of the irradiation device of the present invention;

FIG. 2 is an enlarged partial cross-sectional view showing one end wall of the device of FIG. 1 with fibers embedded therein;

FIG. 3 is a schematic illustrating a method for treating a body fluid of a patient using the device and system of the present invention;

FIG. 4 is a perspective view, with some portions cut away and some parts shown in cross-section of a second embodiment of the irradiation device of the present invention;

FIG. 5 is an enlarged cross-section taken along line 5—5 of FIG. 4;

FIG. 6 is a partial view showing the details of construction of the ends of the casing of the device of FIG. 4;

FIG. 7 is a greatly enlarged cross-sectional view of a single radiant energy transmitting element secured in an end wall of the device of FIG. 1; and FIG. 8 is a view similar to that of FIG. 7 wherein the outer peripheral surface of the single radiant energy transmitting element is coated with a material whose refractive index is less than the refractive index of the element itself.

DETAILED DESCRIPTION OF THE INVENTION

Referring now to the drawings, and especially to FIGS. 1 and 2 thereof, there is shown a device 10 for the transmission of radiant energy from an external source thereof to the interior of said device and for the distribution of said radiant energy within said device to effect radiation of fluids contained therein or flowing therethrough. Device 10 includes a hollow casing 12, which preferably has enlarged end portions and is circular in cross-section, and which has end walls 14 and 16. A bundle 17 of fibers 18 which are adapted to transmit radiant energy into the interior of the casing from an external source thereof, is disposed within casing 12. Fibers 18 may be either solid or hollow. As seen most clearly in FIG. 2, the end portions of all the fibers 18 at one end of the bundle 17 of fibers are secured in end wall 14. Similarly, the end portions of all the fibers 18 at the other end of the bundle 17 of fibers are secured in end wall 16. Securing of the end portions of the fibers in the respective end walls of the irradiating device may be readily accomplished by manual or mechanized potting operations already known in the art. As illustrated in FIG. 2, it is preferred that the ends of the fibers be flush with the outer end surface of the end wall in which they are secured. Device 10 also contains an inlet 20 for the introduction of fluids to be irradiated and an outlet 21 for the withdrawal of the irradiated fluids. The inlet and outlet are disposed in the peripheral wall of casing 12 between end walls 14 and 16. Preferably, inlet 20 is disposed in the enlarged end portion of casing 12 relatively near one of the end walls, e.g., 14. Outlet 21 is preferably located in the enlarged portion of casing 12 relatively near the other end wall, e.g., 16.

The material from which casing 12 is constructed must be structurally and chemically resistant to the type of radiant energy with which it will ultimately be used. For example, where the device is to be used to transmit and distribute ultraviolet radiant energy, i.e., energy having a wavelength in the range of about 320 nanometers to about 460 nanometers (hereinafter sometimes referred to as "ultraviolet" or "U.V." light), casing 12 may be constructed, as by molding, from any of a number of well known polymers which are physically and chemically resistant to ultraviolet light. There are many commercially available polymers and copolymers which are resistant to ultraviolet light and can be used to construct casing 12 when use with ultraviolet light is contemplated. Suitable materials for casing 12 include, but are not limited to, acrylic polymers such as polymethyl methacrylate; acrylic copolymers such as styrene-acrylonitrile; polyolefins such as polyethylene and polypropylene which have been suitably stabilized against UV degradation; polyamides such as Nylon 6,6;

poly(2-methylpentene); polysulfones; polyesters, polyether sulfones; polybutylene, and acrylonitrile-butadiene-styrene copolymers.

In order to be suitable for use in the irradiating device of the present invention, fibers 18 must be capable of transmitting the desired radiant energy axially along their length from a source thereof to the interior of casing 12. As indicated above, in order to obtain maximum efficiency the refractive index of the outer peripheral surfaces of the end portions of the fibers must be equal to or greater than the refractive index of the material which contacts said outer peripheral surfaces when the fibers are secured in the end wall. Thus, in the specific embodiment under discussion, fibers which are made from a material whose refractive index is equal to or greater than the refractive index of the end wall in which the fibers are secured are preferrred. Alternatively, the outer peripheral surfaces of the end portions of the fibers may be treated to provide the necessary refractive index.

Other factors being equal, the outside diameter of the fibers should be as small as possible so as to provide the greatest possible surface area from which radiation may be emitted for distribution of radiant energy within the device. As will be seen hereinafter, irradiating devices in accordance with the present invention have been made with fibers whose outside diameters were about 508 microns and about 350 microns. The outside diameter of the fibers may be generally uniform along the length of the fibers or may vary either periodically or aperiodically, that is, the cross-sectional area of the fibers may vary along their length. It will be understood that the number of fibers used will depend on the size of the interior of casing 12, the outside diameter of the fibers, and the amount of fiber surface area needed within the casing for the emission of radiant energy. For example, irradiating devices in accordance with the present invention have been made by potting 5000 fibers having a generally uniform outside diameter of about 356 microns in a circular casing having an intermediate portion whose diameter is about 1 ¼ inches (3.12 cm). This device provides about 0.85 square meter of fiber surface in the interior of the casing from which radiant energy can be emitted, assuming the effective length of the fibers within the casing is about 6 inches (about 15.24 cm). The amount of radiant energy transmitted into the device and emitted from the fibers in the interior thereof will increase as the number of fibers is increased, other factors being constant. Devices comprising relatively few fibers, e.g., twenty-five or so, would find utility in, e.g., a research laboratory. Other devices, depending on the intended end use, the diameter of the fibers, the size of the casing, etc., may contain anywhere from several hundreds of fibers to many thousands of fibers. Devices of the latter type can be used for sterilizing fluids, for carrying out photo-induced chemical reactions or structural rearrangements, or for extracorporeally irradiating body fluids such as blood or lymph.

The fibers are preferably solid in form but may be hollow if desired. Hollow fibers may have a continuous lumen running the length thereof or may have hollow portions located in discontinuous fashion along their length.

EXAMPLE I

A radiant energy transmitting cell was made in which the elements for transmitting radiant energy were a bundle of approximately two hundred fifty (250) solid monofilament fibers extruded from poly-(2-methylpentene). The end portions of the fibers at each end of the fiber bundle were secured in first and second end walls to form the cell. The poly-(2-methylpentene) fibers which were employed were about 8 inches (about 20.32 centimeters) long and had a refractive index of 1.47. Their outside diameter was approximately 500 microns. The cell was provided with end walls by manually potting the ends of the fibers at each end of the fiber bundle with a silicone potting composition having a refractive index of 1.43, i.e., the refractive index of the potting compound was less than the refractive index of the fibers. After suitable curing of the potting compound, the ends of the potted portions were cut so that the ends of the fibers secured therein were flush with the end walls of the cell. The end walls of the finished cell were about 0.4 inch (about 1.0 centimeter) in diameter and about 0.4 inch (about 1.0 centimeter) thick. The completed radiant energy transmitting cell was carefully mounted between two sources of ultraviolet radiant energy whose predominant wavelength was about 366 nanometers. The energy sources employed were Model B-100A BLak-Ray* Ultraviolet Lamps available commercially from Ultraviolet Products, Inc. The UV radiant energy from these lamps was directed generally perpendicular onto the end walls of the cell. When the UV energy sources were activated, and a 0.01% by weight aqueous solution of Uranil sodium was placed very near to, but not in contact with, the outer surfaces of the fibers in the cell, no fluorescence of the Uranil sodium solution was observed. It was concluded that no UV energy was being emitted from the outer peripheral surfaces of the fibers of the cell. When the aqueous solution of Uranil sodium was brought into contact with the outer surfaces of the fibers in the cell, a brilliant green fluorescence of the Uranil sodium solution was observed. It was concluded that the UV radiant energy being directed onto the end walls of the cell had been transmitted by the fibers of the cell and was being emitted from the outer peripheral surfaces of the fibers when those fibers were contacted by the Uranil sodium solution.

When the energy from a single UV radiant energy source was directed onto one of the end walls of the cell (but not the other), and the dilute Uranil sodium solution was applied to the outer end surface of the other end wall of the cell, a brilliant green fluorescence was again observed. It was concluded that the ultraviolet radiant energy directed at the one end wall of the cell had been transmitted by the fibers in a direction parallel to their longitudinal axis and was being emitted at the outer end surface of the other end wall of the cell.

As noted above, no ultraviolet radiant energy was detected being emitted from the outer peripheral surfaces of the fibers when the dilute Uranil sodium solution was brought very near to, but not in contact with, the outer surfaces of the fibers. While not wishing to be bound by any particular theory of operation, it was believed that the reason for detecting the emission of ultraviolet radiant energy from the outer peripheral surfaces of the fibers when they were actually contacted with the Uranil sodium solution was that the application of that solution to the outer surfaces of the fibers provided, apparently owing to differences in the optical properties between the fiber surfaces and the Uranil sodium solution, paths or "leak points" at which radiation could be radially emitted from the fibers.

The arrangement of radiant energy transmitting fibers after they have been secured in end wall 14 of the cell described in this Example I is illustrated in cross-section in FIG. 7. It will be noted that the outer peripheral surface 15 of the end portion of fiber 18 is directly contacted by the material comprising end wall 14. The refractive index (1.43) of the silicone potting compound used to form the end wall (and hence the refractive index of the end wall itself) is lower than the refractive index (1.47) of the fiber. The arrangement of the fibers in end wall 16 of the cell is identical.

A modified arrangement of radiant energy transmitting fibers in an end wall is illustrated in cross-section in FIG. 8. It will be noted that the outer peripheral surface 15 of the end portion of fiber 18 is coated with a thin layer of material 19, e.g. polyvinylidene fluoride, whose refractive index is equal to or lower than the refractive index of the fiber. Thus the outer peripheral surface of the end portions of fibers 18 which are secured in the end wall are contacted by a material whose refractive index is equal to or lower than the refractive index of the fiber. In such case the refractive index of the material from which the end wall 14 is made is no longer critical; it may be greater than, equal to, or less than, the refractive index of the fibers themselves.

EXAMPLE II (Comparative)

A radiant energy transmitting cell identical to the cell described in Example I above was constructed, except that a polyurethane potting compound having a refractive index of 1.59 was used in place of the silicone potting compound used in the cell of Example I. The completed radiant energy transmitting cell was carefully mounted so that the energy from a UV radiant energy source could be directed at one of its end walls. When the UV radiant energy source was activated and a UV meter was used as a detecting device, no radiant energy could be detected being emitted from the opposite end wall of the cell, nor could any ultraviolet radiant energy be detected being emitted from the outer peripheral surfaces of the fibers in the fiber bundle. Even when radiant energy was directed at both end walls of the cell, no radiant energy could be detected being emitted from the outer peripheral surfaces of the fibers. The results of this Example II and the results observed in Example I demonstrate that where the refractive index of the material contacting the outer peripheral surfaces of the radiant energy transmitting elements secured in the end wall at which the radiant enerov is directed is greater than the refractive index of the fibers themselves, that radiant energy is neither transmitted along the radiant energy transmitting elements to the opposite end wall of the cell nor is it emitted from the outer peripheral surfaces of the elements between the end walls.

EXAMPLE III

An irradiating device 10 in accordance with the present invention was made from a generally circular casing molded from a commercially available styrene/acrylic copolymer resin. The casing was about eight inches (about 20.32 cm.) long. The diameter of the intermediate portion of the casing was about 1¼ inches (about 3.12 cm.) while the enlarged portions at the ends thereof had a diameter of about 1½ inches (about 3.81 cm.). Approximately 300 poly(methyl methacrylate) hollow fibers were inserted into the casing with their ends projecting at each end of the casing. These hollow fibers were manually potted in the casing using a silicone potting compound available from Dow Corning Company as MDX 4-4210 and having a refractive index of 1.43. The UV-T hollow fibers had a continuous lumen extending the length thereof, an outside diameter of approximately 250 microns, and a wall thickness of approximately 25-35 microns. The refractive index of the fibers was 1.45. The effective length of the fibers within the casing after the potting operation was completed was about 6 inches (about 15.24 cm.). Upon completion of the potting and curing steps, the potted portions at both ends of the irradiating device was cut so that the ends of the fibers at both ends of the fiber bundle were flush with the outer end surfaces of the respective end walls formed by the potting operation. Referring to the right-hand side of FIG. 3, the completed device was mounted between two sources 30, 32 (same as used in Example I) of ultraviolet radiant energy whose predominant wavelength was about 366 nanometers. The UV radiant energy was directed generally perpendicularly to the end walls of the irradiating device. Cone-shaped collimators 40 made of aluminum and having fins 42 (also made of aluminum) for dissipation of heat were placed as illustrated between the sources 30, 32 of ultraviolet radiant energy and the walls of the device. A closed loop for recirculation of a ten percent by weight solution in water of the monomer 2-acrylamido-2-methyl propanesulfonic acid (AMPS) was set up. The AMPS solution was continuously circulated with the aid of a pump from a closed container to the inlet of the irradiating device and through the device itself where it passed over the outer peripheral surfaces of the fibers in the fiber bundle. The circulating solution was withdrawn from the irradiating device through the outlet thereof and returned to its closed container. The entire set-up was run under nitrogen at ambient pressure and temperature.

The ultraviolet energy sources were activated and the ten percent by weight AMPS solution in water was continuously circulated through the system. Samples of the circulating solution were withdrawn from the system after the first 15 minutes, then at 30 minute intervals up to 90 minutes. A visually observable increase in the viscosity of the circulating solution was noted at the end of 30 minutes. The experiment was terminated after 90 minutes. Number average molecular weights were determined on the withdrawn samples using high pressure liquid chromotography with an integrating computer for calculating molecular weight. The following results were obtained:

| Sample | Elapsed Time, Minutes | Number Average Molecular Weight |
| --- | --- | --- |
| 1. | 0 | (Monomer) |
| 2. | 15 | 26,400 |
| 3. | 30 | 25,800 |
| 4. | 60 | 381,000 |
| 5. | 90 | 381,000 |

The solid material recovered by evaporation of the irradiated AMPS solution was identified by infrared analysis to be poly-(2-acrylamido-2-methyl) propanesulfonic acid.

The foregoing molecular weight data and infrared analysis result, as well as the visually observed increase in the viscosity of the circulating AMPS solution, demonstrate that the monomeric AMPS was polymerized.

Since it is known that AMPS can be photo-polymerized under the influence of ultraviolet radiant energy, it was concluded that the ultraviolet radiant energy directed onto the end walls of the device by the externally located sources 30, 32 was transmitted by the hollow fibers into the interior of the irradiating device where it was subsequently emitted from the surfaces of the fibers to effect irradiation of the circulating solution.

It will be noted that each of the fibers used in this Example III has a first end, a first end portion adjacent said first end, a second end, a second end portion adjacent said second end, and an intermediate portion between the first end portion and the second end portion. In the completed irradiating device, the respective first ends of the fibers are flush with the outer surface of one of the end walls, while the respective second ends of the fibers are flush with the outer surface of the other of the end walls. The first end portions of the fibers are secured in one of the end walls, while the second end portions of the fibers are secured in the other end wall. The respective intermediate portions of the fibers are disposed within the interior of the casing where they extend between the inner surfaces of the two end walls.

EXAMPLE IV (Comparative)

An experiment using the identical apparatus and procedure described in Example III was conducted but no ultraviolet radiant energy was used. Samples taken periodically were subjected to high pressure liquid chromatography analysis. No evidence of polymerization was observed after 90 minutes.

EXAMPLE V

The experiment described in Example III was repeated. An increase in viscosity was again visually observed after the AMPS solution had been circulated for 30 minutes. The experiment was terminated after 90 minutes at which time a viscous solution having a viscosity of 30,000 centipoises, as determined on a Brookfield viscometer, had been obtained. The number average molecular weight of the polymer recovered from the solution was determined to be 421,000.

EXAMPLE VI

Another irradiating device 10 in accordance with the present invention was constructed using a casing 12 described in Example III. Five thousand (5,000) solid monofilament acrylic fibers were extruded from Cyro 7N Clear resin commercially available from Cyro Industries, Inc. and were placed in the casing. These fibers had an outside diameter of about 0.014 inch (about 356 microns) and a refractive index of 1.47. The fibers were manually potted in the casing using the silicone potting compound described in Example III hereof. It will be understood that the fibers can be potted using well-known mechanized processes, such as those described generally in U.S. Pat. No. 3,442,002 (Geary et al) or U.S. Pat. No. 4,289,623 (Lee). After the potting compound was cured, the potted portions at each end of the device were cut so that the respective fiber ends embedded therein were flush with the outer end surface of the potted end wall. The completed irradiating device was mounted between ultraviolet radiant energy sources 30, 32 and collimators 40 as illustrated in the right-hand side of FIG. 3 of the drawings. A closed loop for the circulation of fluids through the device was set up in the manner already described in Example III.

An aqueous solution of Uranil sodium (0.01% by weight) was circulated through the device and the two radiant energy sources (same as those described earlier herein) were activated. The predominant wavelength of the ultraviolet energy emitted from the sources was 366 nanometers. A brilliant green fluorescence was observed in the Uranil sodium solution circulating through the irradiating device. It was concluded that the radiant energy from the external radiant energy sources was being transmitted via the fibers into the interior of the device where it was then emitted from the outer surfaces of the fibers to irradiate the Uranil sodium solution circulating therethrough.

After the device and circulating loop were thoroughly flushed, the UV radiant energy sources were again activated and a 10% by weight solution in water of 2-acrylamido-2-methyl propanesulfonic acid (AMPS) was circulated through the irradiating device. It was visually observed that the viscosity of the circulating solution increased with time, from which observation it was concluded that the AMPS was being polymerized under the influence of the UV energy being emitted from the outer surfaces of the fibers contacted by the AMPS solution in the interior of the device. A sample of the circulating solution was taken after 60 minutes; the number average molecular weight of the polymer formed was determined to be 408,000.

Referring now to FIGS. 4–6 of the drawings, there is shown a second embodiment of an irradiating device in accordance with the present invention. Device 50 comprises an elongated, generally cylindrical casing 54 having an intermediate reduced diameter portion 53 and enlarged end portions 51, 52. The device further includes a bundle 17 of individual fibers 18, the longitudinal axes of these fibers being parallel to the longitudinal axis of the device itself. The fibers are potted in the end walls of the device in the manner as described earlier herein in connection with device 10. Device 50 further includes an inlet 20 and an outlet 21, inlet 20 being located in enlarged end portion 51 inwardly of end wall 14 and outlet 21 being located in enlarged end portion 52 inwardly of the other end wall of the device.

In order to provide more uniform distribution of fluids entering and leaving the device, and in order to help prevent "channeling" of fluids flowing through the device, baffles 55 are provided at each end of the device. These baffles lie adjacent inlet 20 and outlet 21; are concentric with, and smaller in diameter than, the enlarged end portions 51 and 52 of the casing; and in the preferred embodiment comprise extensions of the reduced diameter, intermediate wall portion 53 of the casing. Thus, as can be seen most clearly in FIG. 5, there is a small annular clearance 58 between the interior surface 56 of enlarged portion 51 and the exterior surface 57 of baffle 55. Baffle 55 includes a plurality of notched portions 60 which, in the preferred embodiment, are v-shaped and four in number. The portion of the baffle directly opposite the inlet and outlet must not carry a notch inasmuch as such an arrangement would defeat the very purpose of the baffle which is to provide for more uniform distribution of fluid and to help prevent undesirable channeling of the same while it is flowing through the device. It will be understood that the described baffling is constructed and arranged identically at both ends of the device.

As can be seen by reference to FIG. 4, the end portion of baffle 55 extends beyond the area beneath inlet 20 a short distance into potted end wall 14. While the optimum utilization of the flow access areas provided by a given number of notched portions 60 will be obtained when end edge 61 of baffle 55 abuts the interior face 62 of potted end wall 14 in leak proof relationship, this is difficult to achieve as a practical matter. In order then to maximize the utilization of the flow access areas provided by notched portions 60, the distance by which the end of the baffle extends into the potted end wall should be kept to a minimum consistent with ensuring adequate sealing. It will be clear that if the distance by which the baffle extends into the potted end wall is too great, the notched portions will be partially occluded, in which case the efficiency of fluid distribution is reduced, or the notched portions can become completely occluded, in which case the fluid entering the inlet cannot be distributed within the casing at all.

In some instance, the material employed to pot the fiber bundle and form the end walls of device 10 or device 50 may have less than adequate adhesion to the interior surfaces of the enlarged end portions of the device. If this occurs, it is possible that fluid entering through inlet 20 or exiting outlet 21 may leak in the regions of said inadequate adhesion. Such leaking, to the extent it may occur, can be obviated by securing caps 70 to the ends of the device. As seen in FIGS. 4 and 5, cap 70 has an end portion 71 and a skirt portion 72. The cap can be molded from a plastic material, preferably the same plastic as that used for casing 12, and which is readily sealable, for example by the use of ultrasonic welding, an adhesive or the like, to the casing and the end walls of the device. The thickness of the cap can conveniently be about 5 mm. As shown in FIGS. 4 and 5, cap 70 is placed over the ends of device 50. The interior surface of skirt portion 72 (which can conveniently be about 13 mm.) of cap 70 is brought into contact with the outer surface of enlarged end portion 51 while the interior surface of cap end portion 71 is brought into contact with the outer end surface of end wall 14 in the regions thereof which are inwardly adjacent the peripheral end edge of enlarged portion 51 of the casing. Sealing of cap 70 to the adjoining surfaces can be effected, for example, by ultrasonic welding, by heat treatment or by the use of a suitable adhesive. When the cap has been sealed as described, any leakage due to poor adhesion between the potted end wall 14 and the enlarged portion 51 of the device will be eliminated. Preferably the cap should be transparent to the radiant energy to be used with the device. If, however, the material selected for the cap absorbs radiant energy of the kind which is to be employed with the device, an interior portion 74 of the cap 70 can be cut out prior to the sealing operation. This allows the radiant energy to be directed at the end wall of the device through the cut-out portion without absorption of the radiant energy by the material comprising the cap. The remaining peripheral portion of end portion 71 of cap 70 is available for sealing to the potted end wall as described earlier.

Devices in accordance with the present invention may also be provided with a plurality of lugs on their outer surface. The purpose of these lugs is to provide means by which casing 12 may be securely held during a mechanized potting operation or thereafter during actual use of the device itself. In the embodiment illustrated in FIGS. 4 and 6, there are four lugs 75 at each end of casing 12. The lugs, whose number may be varied, are generally semicircular in shape and are located on the enlarged end portions outwardly (i.e. toward the ends of casing 50) of inlet 20 and outlet 21.

1. A device for irradiating a fluid contained therein or flowing therethrough, said device comprising:
 a hollow casing having a first end wall and a second end wall,
 an inlet in said casing between said first end wall and said second end wall for introducing said fluid into the interior of said casing,
 an outlet in said casing between said first end wall and said second end wall for withdrawing said fluid from the interior of said casing,
 at least one radiant energy transmitting element having a first end portion and a second end portion being disposed within said casing, said radiant energy transmitting element being adapted to transmit radiant energy to the interior of said casing from a radiant energy source located externally of said device and to emit radiant energy in the interior of said casing when contacted by said fluid,
 the first end portion of said element being secured in said first end wall, the outer peripheral surface of said end portion of said element which is secured in said end wall being contacted by a material whose refractive index is equal to or less than the refractive index of said element.

2. A device according to claim 1 including a plurality of said radiant energy transmitting elements.

3. A device according to claim 1 or 2 wherein said radiant energy transmitting elements are in the form of fibers.

4. A device according to claim 1 or 2 wherein said radiant energy transmitting elements are in the form of solid fibers.

5. A device for irradiating a fluid contained therein or flowing therethrough, said device comprising:
 a hollow casing having a first end wall and a second end wall,
 an inlet in said casing between said first end wall and said second end wall for introducing said fluids into the interior of said casing,
 an outlet in said casing between said first end wall and said second end wall for withdrawing said fluid from the interior of said casing,
 at least one radiant energy transmitting element having a first end portion and a second end portion being disposed within said casing, said radiant energy transmitting element being adapted to transmit radiant energy to the interior of said casing from a radiant energy source located externally of said device and to emit radiant energy in the interior of said casing when contacted by said fluid,
 the first end portion of said element being secured in said first end wall, the outer peripheral surface of said first end portion of said element which is secured in said first end wall being contacted by a material whose refractive index is equal to or less than the refractive index of said element,
 the second end portion of said element being secured in said second end wall.

6. The device according to claim 5 including a plurality of said radiant energy transmitting elements.

7. A device according to claim 5 wherein the outer peripheral surface of said second end portion of said element which is secured in said second end wall is contacted by a material whose refractive index is equal to or less than the refractive index of said element.

8. A device according to claim 7 including a plurality of said radiant energy transmitting elements.

9. A device according to any one of claims 5 through 8 in which said radiant energy transmitting elements are in the form of fibers.

10. An apparatus for irradiating a fluid comprising
(a) a device including:
a hollow casing having a first end wall and a second end wall,
an inlet in said casing between said first end wall and said second end wall for introducing said fluid into said casing,
an outlet in said casing between said first end wall and said second end wall for withdrawing said fluid from said casing,
at least one radiant energy transmitting element being disposed within said casing, said radiant energy transmitting element being adapted to transmit radiant energy to the interior of said casing from a radiant energy source located externally of said device and to emit radiant energy in the interior of said casing when contacted by said fluid said element having a first end, a first end portion adjacent said first end, a second end, and a second end portion adjacent said second end,
the first end portion of said element being secured in said first end wall, the outer peripheral surface of said end portion of said element which is secured in said first end wall being contacted by a material whose refractive index is equal to or less than the refractive index of said element; and
(b) means cooperatively associated with said device for directing radiant energy onto said first end of said element so that said radiant energy is transmitted axially of said element into the interior of said casing.

11. Apparatus according to claim 10 in which there are a plurality of said radiant energy transmitting elements within said casing.

12. Apparatus according to claim 10 or 11 wherein said radiant energy transmitting elements are selected from the group consisting of fibers, rods, and rectangular plates.

13. Apparatus according to claim 10 or 11 wherein said radiant energy transmitting elements are in the form of fibers.

14. Apparatus according to claim 10 or 11 wherein said radiant energy transmitting elements are in the form of solid fibers.

15. A method for irradiating a fluid comprising the steps of
(a) providing a device comprising a hollow casing having a first end wall, a second end wall, an inlet for introducing said fluid into the interior of said casing, an outlet for withdrawing said fluid from the interior of said casing, and at least one radiant energy transmitting element disposed within said casing, said radiant energy transmitting element being adapted to transmit radiant energy to the interior of said casing from a radiant energy source located externally of said device and to emit radiant energy in the interior of said casing when contacted by said fluid, said element having a first end, a first end portion adjacent said first end, a second end, and a second end portion adjacent said second end, the first end portion of said element being secured in said first end wall, the outer peripheral surface of said end portion of said element which is secured in said first end wall being contacted by a material whose refractive index is equal to or less than the refractive index of said element,
(b) directing radiant energy onto said first end of said element so that said radiant energy is transmitted axially of said radiant energy transmitting element into the interior of said casing,
(c) introducing said fluid into the interior of said casing, and
(d) withdrawing said fluid from the interior of said casing.

16. A method according to claim 15 wherein said fluid to be irradiated is circulated through said device.

17. A method according to claim 15 wherein said device includes a plurality of elements adapted to transmit radiant energy.

18. A method according to claim 15 wherein said radiant energy is ultraviolet radiant energy.

19. A method according to claim 15 wherein said fluid to be irradiated is circulated through said device and said device includes a plurality of elements adapted to transmit radiant energy.

20. A method according to claim 15 wherein said fluid to be irradiated is circulated through said device and said radiant energy is ultraviolet radiant energy.

21. A method according to claim 15 wherein said device includes a pluraltiy of elements adapted to transmit radiant energy and said radiant energy is ultraviolet radiant energy.

22. A method according to claim 15 wherein said fluid to be irradiated is circulated through said device, said device includes a plurality of elements adapted to transmit radiant energy, and said radiant energy is ultraviolet radiant energy.

23. A method according to any one of claims 15 through 22 wherein said elements adapted to transmit radiant energy are in the form of fibers.

24. A method for irradiating a fluid comprising the steps of:
(a) providing a device comprising a hollow casing having a first end wall, a second end wall, an inlet for introducing said fluid into the interior of said casing, an outlet for withdrawing said fluid from the interior of said casing, and a plurality of fibers adapted to transmit radiant energy to the interior of said casing from a radiant energy source located externally of said device and to emit radiant energy in the interior of said casing when contacted by said fluid, each of said fibers haivng a first end, a first end portion adjacent said first end, a second end, a second end portion adjacent said second end, and an intermediate portion between said first end portion and said second end portion, the intermediate portions of said fibers being disposed within said casing, the respective first end portions of said plurality of fibers being secured in said first end wall, the outer peripheral surfaces of said first end portions of said fibers which are secured in said first end wall being contacted by a material whose refractive index is equal to or less than the refractive index of said plurality of fibers,
(b) directing radiant energy onto at least the respective first ends of said fibers, so that radiant energy is transmitted axially of said fibers into the interior of said casing,
(c) introducing said fluid into the interior of said casing, and
(d) withdrawing said fluid from the interior of said casing.

25. A method according to claim 24 wherein the fluid to be irradiated is circulated through said device.

26. A method according to claim 24 wherein said radiant energy is ultraviolet radiant energy.

27. A method according to claim 24 wherein the fluid to be irradiated is circulated through said device and said radiant energy is ultraviolet radiant energy.

28. A method according to any of claims 24 through 27 in which radiant energy is directed onto the respective second ends of the fibers.

29. A method for irradiating a fluid comprising the steps of:
  (a) providing a device comprising a hollow casing having a first end wall, a second end wall, an inlet for introducing said fluid into the interior of said casing, an outlet for withdrawing said fluid from the interior of said casing, and a plurality of fibers adapted to transmit radiant energy to the interior of said casing from a radiant energy source located externally of said device and to emit radiant energy in the interior of said casing when contacted by said fluid, each of said fibers having a first end, a first end portion adjacent said first end, a second end, a second end portion adjacent said second end, and an intermediate portion between said first end portion and said second end portion, the intermediate portions of said fibers being disposed within said casing, the respective first end portions of said plurality of fibers being secured in said first end wall, the outer peripheral surfaces of said first end portions of said fibers which are secured in said first end wall being contacted by a material whose refractive index is equal to or less than the refractive index of said plurality of fibers, the respective second end portions of said fibers being secured in said second end wall,
  (b) directing radiant energy onto at least the respective first ends of said fibers, so that radiant energy is transmitted axially of said fibers into the interior of said casing,
  (c) introducing said fluid into the interior of said casing, and
  (d) withdrawing said fluid from the interior of said casing.

30. A method according to claim 29 wherein the fluid to be irradiated is circulated through said device.

31. A method according to claim 29 wherein said radiant energy is ultraviolet radiant energy.

32. A method according to claim 29 wherein the fluid to be irradiated is circulated through said device and said radiant energy is ultraviolet radiant energy.

33. A method according to any of claims 29 through 32 wherein radiant energy is directed onto the respective second ends of said fibers.

34. A device according to claim 1 or 2 wherein said radiant energy transmitting elements are in the form of hollow fibers.

35. A device according to claim 8 wherein said radiant energy transmitting elements are in the form of solid fibers.

36. A device according to claim 8 wherein said radiant energy transmitting elements are in the form of hollow fibers.

37. A device according to claim 1 or 5 wherein said radiant energy transmitting elements comprise at least several hundred fibers.

38. A device according to claim 1 or 5 wherein said radiant energy transmitting elements comprise at least about five thousand fibers.

39. A device according to claim 37 or 38 wherein said fibers are solid fibers.

40. Apparatus according to claim 10 or 11 wherein said radiant energy transmitting elements are in the form of hollow fibers.

41. Apparatus according to claim 10 wherein said radiant energy transmitting elements are in the form of fibers and there are at least several hundred such fibers.

42. Apparatus according to claim 10 wherein said radiant energy transmitting elements are in the form of fibers and there are at least about five thousand such fibers.

43. Apparatus according to claim 41 or 42 wherein said fibers are solid fibers.

44. A method according to claim 15 wherein the radiant energy transmitting elements which comprise said device are in the form of fibers and there are at least several hundred such fibers.

45. A method according to claim 15 wherein the radiant energy transmitting elements which comprise said device are in the form of fibers are there are at least five thousand such fibers.

46. A method according to claim 44 or 45 wherein said fibers are solid fibers.

47. A method according to claim 22 wherein said fibers are solid.

48. A method according to claim 22 wherein said fibers are hollow.

49. A method according to claim 24 in which said device includes at least several hundred of said fibers.

50. A method according to claim 24 in which said device includes at least about five thousand said fibers.

51. A method according to claim 50 or 51 in which said fibers are solid fibers.

52. A method according to any one of claims 29 through 32 wherein the outer peripheral surfaces of said second end portions of said fibers which are secured in said second end wall are contacted by a material whose refractive index is equal to or less than the refractive index of said plurality of fibers and said radiant energy is directed onto the respective second ends of said fibers.

53. A method according to any one of claims 29 through 32 in which said device includes at least several hundred of said fibers.

54. A method according to claim 53 wherein said fibers are solid fibers.

55. A method according to any one of claims 29 through 32 in which said device includes at least about five thousand of said fibers.

56. A method according to claim 55 wherein said fibers are solid fibers.

* * * * *

UNITED STATES PATENT AND TRADEMARK OFFICE
CERTIFICATE OF CORRECTION

PATENT NO. : 4,467,206

DATED : August 21, 1984

INVENTOR(S) : John A. Taylor and Richard F. Conyne

It is certified that error appears in the above-identified patent and that said Letters Patent is hereby corrected as shown below:

Claim 10, line 21: "energyin" should read --energy in--.

Claim 45, line 30: "are there" should read --and there--.

Signed and Sealed this

Sixteenth Day of December, 1986

Attest:

DONALD J. QUIGG

Attesting Officer

Commissioner of Patents and Trademarks